US008377658B2

(12) United States Patent
Kim et al.

(10) Patent No.: US 8,377,658 B2
(45) Date of Patent: Feb. 19, 2013

(54) PROCESS FOR MANUFACTURING TAGATOSE USING SOY OLIGOSACCHARIDE

(75) Inventors: Seong-Bo Kim, Seoul (KR); Jung-Hoon Kim, Seoul (KR); Young-Mi Lee, Seoul (KR); Jin-Ha Kim, Gyeonggi-do (KR); Seung-Won Park, Gyeonggi-do (KR); Kang-Pyo Lee, Seoul (KR)

(73) Assignee: CJ Cheiljedang Corporation, Seoul (JP)

( * ) Notice: Subject to any disclaimer, the term of this patent is extended or adjusted under 35 U.S.C. 154(b) by 268 days.

(21) Appl. No.: 12/812,567

(22) PCT Filed: Jan. 28, 2009

(86) PCT No.: PCT/KR2009/000392
§ 371 (c)(1),
(2), (4) Date: Jul. 12, 2010

(87) PCT Pub. No.: WO2009/096693
PCT Pub. Date: Aug. 6, 2009

(65) Prior Publication Data
US 2010/0285539 A1 Nov. 11, 2010

(30) Foreign Application Priority Data
Jan. 28, 2008 (KR) .................. 10-2008-0008717

(51) Int. Cl.
*C12P 19/24* (2006.01)
(52) U.S. Cl. ............. 435/94; 435/72; 435/201; 435/208
(58) Field of Classification Search ............... 435/72, 435/201, 208, 94
See application file for complete search history.

(56) References Cited

U.S. PATENT DOCUMENTS

| | | | |
|---|---|---|---|
| 3,894,913 A | 7/1975 | Watanabe et al. | |
| 3,957,578 A * | 5/1976 | Narita et al. | 435/208 |
| 4,273,922 A | 6/1981 | Hicks | |
| 4,663,449 A | 5/1987 | Barker et al. | |
| 5,002,612 A | 3/1991 | Beadle et al. | |
| 5,078,796 A | 1/1992 | Beadle | |
| 6,057,135 A | 5/2000 | Ibrahim et al. | |
| 6,797,309 B2 | 9/2004 | Monagle | |
| 2002/0039619 A1 | 4/2002 | Monagle | |
| 2003/0175909 A1 | 9/2003 | Kim et al. | |
| 2005/0161401 A1 * | 7/2005 | Heikkila et al. | 210/656 |
| 2009/0004642 A1 * | 1/2009 | Magaletta et al. | 435/4 |
| 2009/0306366 A1 | 12/2009 | Kim et al. | |

FOREIGN PATENT DOCUMENTS

| | | |
|---|---|---|
| EP | 0375046 | 6/1990 |
| KR | 1020010090004 A | 10/2001 |
| KR | 1020020051835 A | 6/2002 |
| KR | 1020060068505 A | 6/2006 |
| KR | 10-2006-0120197 | 11/2006 |
| WO | WO 02-15712 A2 | 2/2002 |
| WO | WO 2005/047510 | 5/2005 |
| WO | WO 2006/058092 | 6/2006 |

OTHER PUBLICATIONS

Lim, B.-C. et al., (Apr. 2007) Biological Society of Korea Conference, 2007 Conference and International Symposium, pp. 25-25, u Korea Society for Biotechnology (with English translation of publication date); also available at http://www.earticle.net/Article.aspx?sn=99490; last accessed Apr. 24, 2012.
International Search Report mailed Sep. 8, 2009 in PCT/KR2009/000392.
Written Opinion mailed Sep. 8, 2009 in PCT/KR2009/000392.
Ekeberg et al. (2002) Carbohydrate Research 337:779-786, "Base catalysed isomerisation of aldoses of the *arabino* and *lyxo* series in the presence of aluminate".
Kim and Oh. (2005) J. Biotech. 120(2):162-73, "Purification and characterization of an L-arabinose isomerase from an isolated strain of Geobacillus thermodenitrificans producing D-tagatose".
Lee et al. (Mar. 2004) Appl. Environ. Microbiol. 70:1397-1404, "Characterization of a Thermostable L-Arabinose (D-Galactose) Isomerase from the Hyperthermophilic Eubacterium Thermotoga maritime".
Oh et al. (2001) Biotechnology Lett. 23, 1859-1862, "Development of an immobilization method of L-arabinose isomerase for industrial production of tagatose".
Tkac et al. (1999) Biotechnology Techniques 13:931-936, "Rapid and sensitive galactose oxidase-peroxide biosensor for galactose detection with prolonged stability".
Yoon et al. (2003) World J. of Microbiology & Biotechnology, 19:47-51, "Properties of L-arabinose isomerase from *Escherichia coli* as biocatalyst for tagatose production".
Green et al. (1956) Journal of Biological Chemistry, 219:557-568, "Enzymatic Conversion of L-Fucose to L-Fuculose".
Cohen (1953) Journal of Biological Chemistry, 201:71-84, "Studies on D-Ribulose and its Enzymatic Conversion to D-Arabinose".
Mitsuhashi et al. (1953) Journal of Biological Chemistry 204:1011-1018, "Conversion of D-Xylose to D-Xylulose in Extracts of Lactobacillus Pentosus".
EP Search Report issued Oct. 29, 2012 in EP 09705280.7.
Jorgensen,et al. (2004) "Enzymatic conversion of D-galactose to D-tagatose: heterologous expression and characterisation of a thermostable L-arabinose isomerase from *Thermoanaerobacter mathranii*," Appl Microbiol Biotechnol, 64:816-822.
Zhan et al., (Jun. 2002) "Preliminary Exploration into How to Extract Sucralose Through Hydrolyzing Raffinose," Beverage & Fast Frozen Food Industry, 8(2):1-6.

* cited by examiner

*Primary Examiner* — Susan Hanley
(74) *Attorney, Agent, or Firm* — Swanson & Bratschun, L.L.C.

(57) ABSTRACT

The present invention relates to a method for producing tagatose using soy oligosaccharide or soluble sugar solution containing the same, more precisely, a method for producing tagatose comprising the following steps; hydrolyzing soy oligosaccharide by using α-galactosidase selectively; producing tagatose continuously by enzymatic isomerization of galactose obtained from the hydrolysate; separating the produced tagatose by chromatography; and recycling the non-reacted materials.

18 Claims, 13 Drawing Sheets

PROCESS FOR MANUFACTURING TAGATOSE USING SOY OLIGOSACCHARIDE

THE CROSS-REFERENCE TO RELATED APPLICATIONS

Incorporation by Reference

The present application is a national phase entry under 35 U.S.C. 371 of International Application No. PCT/KR2009/000392 filed on Jan. 28, 2009, which claims the benefit of Korean Patent Application No. 10-2008-0008717 filed on Jan. 28, 2008. The disclosures of said applications are incorporated by reference herein.

TECHNICAL FIELD

The present invention relates to a method for producing tagatose using soy oligosaccharide or soluble sugar solution containing the same, more precisely, a method for producing tagatose using galactose which is recovered by selective hydrolysis from soluble oligosaccharide in soy.

BACKGROUND ART

Tagatose has the natural sweetness that is hardly distinguished from that of sucrose. The physical properties of tagatose are also very similar to those of sucrose. However, the in-taken tagatose is hard to be absorbed in the small intestine, suggesting that it does not affect blood sugar level. Tagatose is also a low caloric sweetener whose calorie is only about 30% of that of sucrose. Tagatose has a prebiotic effect accelerating the proliferation of beneficial *lactobacillus* through fermenting by rumen microorganisms.

However, this beneficial tagatose is a rare sugar which is not distributed in nature but included in diary products or some plants at a very low concentration. To use tagatose as a low caloric functional sweetener, a novel technique is required to mass-produce tagatose from an inexpensive raw material.

U.S. Pat. No. 5,002,612 and NO 5078796 describe a method for producing D-tagatose, in which lactose or a lactose-containing material is hydrolyzed into galactose and glucose mixture by using lactase and then glucose is eliminated randomly, followed by chemical isomerization of galactose into tagatose.

U.S. Pat. No. 6,057,135 describes a method for producing tagatose comprising the following steps: obtaining galactose and glucose by hydrolyzing cheese whey or milk; isomerizing the obtained galactose by L-arabinose isomerase; and recycling non-converted compounds after the separation of the products and non-converted compounds by chromatography.

The major raw materials which have been used for the production of tagatose so far are milk processing by-products such as lactose or lactose containing materials. In the bioconversion process that uses lactose or lactose containing materials as a starting material, the production of tagatose should be basically performed by two-step reaction (lactose→galactose→tagatose).

DISCLOSURE

Technical Problem

Based on the above facts, the present inventors studied and searched raw materials, except lactose, that contain galactose at a high level among wood and process by-products that can be provided from nature with a low price. Then, the present inventors confirmed that byproducts of isolated soy protein contained high concentration of galactose, compared with other materials, and then selected those appropriate for chromatography. As a result, the present inventors completed this invention by confirming that soy oligosaccharide obtained from isolated soy protein whey was the raw material that could be actually industrialized.

Therefore, it is an object of the present invention to provide a method for producing galactose by selective hydrolysis of soy oligosaccharide or soluble sugar solution containing the same.

It is another object of the present invention to provide a method for producing tagatose comprising the following steps: obtaining an isomerized product by isomerization of galactose in the hydrolyzed sugar solution via enzyme isomerization; and obtaining tagatose by chromatography.

Technical Solution

To achieve the above objects, the present invention provides a method for producing galactose by selective hydrolysis of soy oligosaccharide or soluble sugar solution containing the same as a major component by using alpha-galactosidase.

The present invention also provides a method for producing tagatose comprising the following steps:

1) hydrolyzing soy oligosaccharide or soluble sugar solution containing the same as a major component selectively by using alpha-galactosidase;

2) isomerizing galactose in the hydrolyzed sugar solution by using arabinose isomerase; and 3) obtaining tagatose by serial separation of the isomerized product by using chromatography, and recycling galactose.

The present invention further provides a method for producing tagatose, in which the said step 1) and step 3) are performed simultaneously in the same reactor.

Advantageous Effect

The present inventors developed an efficient method for producing tagatose considering the balance of materials in each step and equipment investment. Particularly, to make the separation by chromatography easy, a novel economic process taking selective hydrolysis has been established. Therefore, the present invention is useful for the efficient production of tagatose, according to the following steps: obtaining galactose not from the conventional lactose but from soy oligosaccharide and soluble sugar solution containing the same as a major component by selective hydrolysis; and producing tagatose by single chromatography of the sugar solution containing at least 3 different sugars (sucrose, galactose, and tagatose) obtained by isomerization of the above galactose.

DESCRIPTION OF DRAWINGS

The above and other objects, features and advantages of the present invention will become apparent from the following description of preferred embodiments given in conjunction with the accompanying drawings, in which:

FIG. 5 and FIG. 6 illustrate the results of the analysis of sugar content in soy oligosaccharide treated with invertase free glycosidase with.

BEST MODE

The present invention provides a method for producing tagatose comprising the following steps:

1) hydrolyzing soy oligosaccharide or soluble sugar solution containing the same as a major component selectively by using alpha-galactosidase;

2) isomerizing of galactose in the hydrolyzed sugar solution by using arabinose isomerase; and 3) obtaining tagatose by serial separation of the isomerized product by using chromatography, and recycling galactose.

The starting material of the present invention can be soy bean whey, the by-product of isolated soy protein, soy oligosaccharide originated therefrom, or soluble sugar solution containing the same as a major component, and soy oligosaccharide is more preferred.

The sugar included in the soy bean whey is mostly sucrose, raffinose and stachyose, and raffinose and stachyose are composed of a polymer in which sucrose and galactose are combined via alpha-1,4 linkage. Carbohydrate components of the said sugars are shown in Table 1. Each unit component of soy bean whey or soy oligosaccharide is sucrose and galactose, or more specifically understood as mixed monosaccharide comprising glucose, fructose and galactose.

TABLE 1

| Carbohydrate name | Glycogen No. | Galactose content | Molar ratio of sugar content |
|---|---|---|---|
| Raffinose | 3 | 33.3 | Suc:D-Gal = 1:1 |
| Stachyose | 4 | 50 | Suc:D-Gal = 1:2 |
| Sucrose | 2 | 0 | — |

In most plant materials found in nature including soy bean whey of the present invention, most of galactose exists in the form of oligosaccharide or carbohydrate with glucose or fructose. So, the sugar solution obtained therefrom by hydrolysis also comprises mixed monosaccharide in which at least three different sugars are included.

The conventional by-product derived from milk is mainly composed of lactose alone. Therefore, when this product is hydrolyzed, mixed monosaccharide comprising glucose and galactose can be easily obtained initially, which can be economically separated by advanced chromatography.

However, the sugar solution containing at least three different sugars like the one of the present invention is not easy to be separated by chromatography unless selective conditions are fulfilled. That is, it is very difficult to produce galactose or tagatose economically from other raw materials than lactose.

In general, separation of sugar by chromatography is performed by taking advantage of difference in weak binding force among metal ions attached on the sugar and ion resin. Particularly, metal ion residues applicable to chromatography for food are limited to K, Na, Ca, and Mg.

Figure 1:
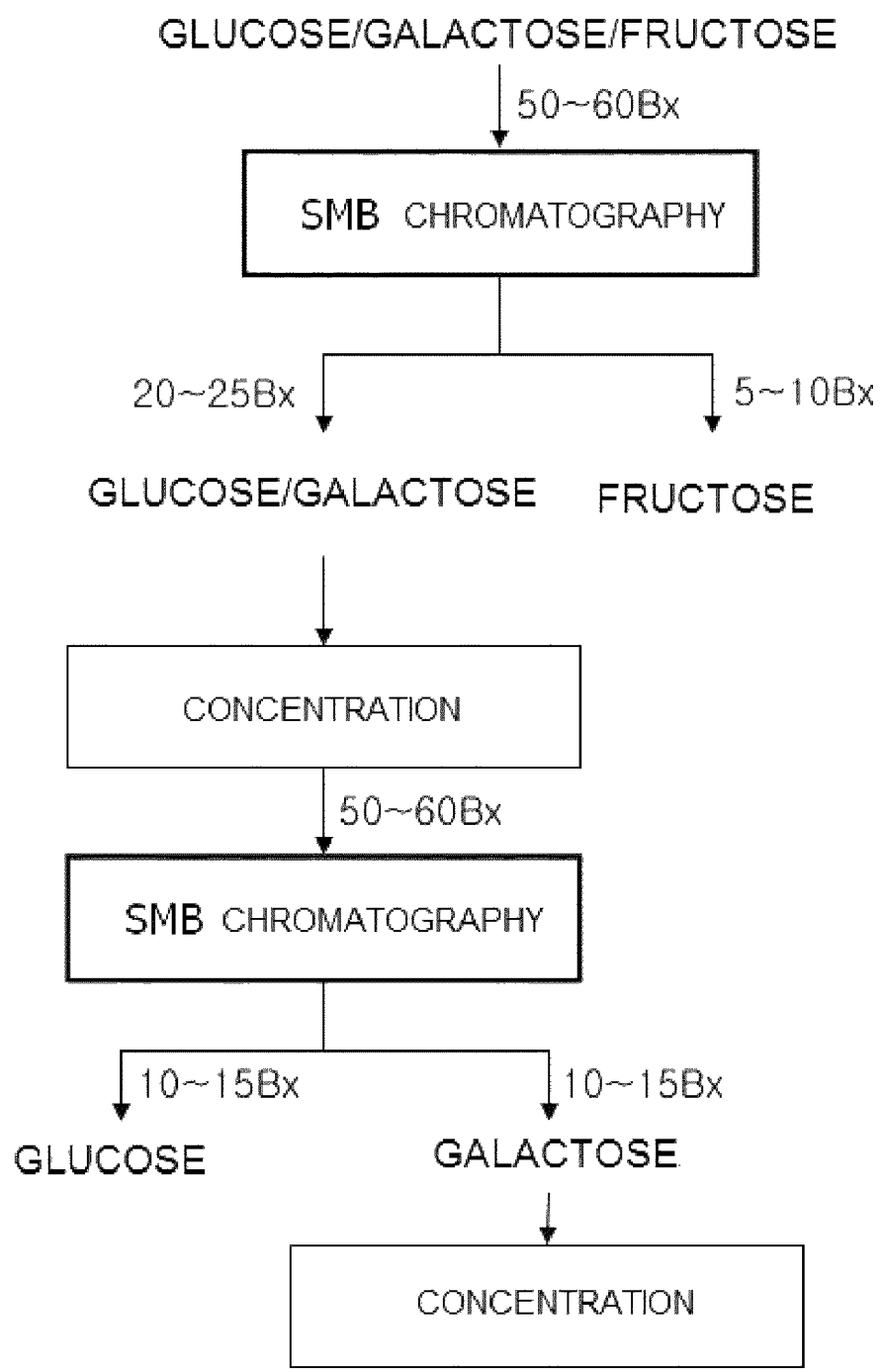
FIG. 1 and FIG. 2 are schematic diagrams illustrating the separation method by pure chromatography of the mixed sugar solution.

Glucose and galactose are very similar in their physical structures composed of aldose form. Fructose is the sugar composed of ketose form. In general, the separation of mixed sugar composed of aldose form and ketose form is performed economically by chromatography using the resin having cation residues, which is actually widely used in starch sugar process. However, to separate glucose and galactose which have same aldose form and similar physical structure, a specific resin having K and Na is necessary. That is, galactose is only pure-separated by using two different chromatography equipments in serial. This process is shown in FIG. 1. The separation of mixed sugar by chromatography uses a large amount of water, suggesting that cost for concentration increases and high priced equipment is required.

The enzyme used for the hydrolysis of the present invention is α-galactosidase, and more preferably invertase free α-galactosidase.

The said α-galactosidase is one of the natural glycolytic enzymes, which can digest selectively alpha-1,4-linkage between sucrose and galactose composing raffinose or stachyose. Therefore, it can be used for the preparation of sugar solution composed of sucrose and galactose as major components from soy bean whey or soy oligosaccharide.

However, to produce an enzyme that is industrially applicable, it is general to obtain supernatant by culturing a microorganism producing the enzyme or mycelia thereof, which is then further used as a raw material for the production of the enzyme. In most cases, the material includes the most representative glycolytic enzyme, invertase. In this invention, the selective hydrolysis for sucrose and galactose is necessary for the convenience of chromatography. Therefore, invertase free α-galactosidase makes the chromatography easier.

The said α-galactosidase is originated from the strain that dose not have the invertase gene inside. More preferably, the α-galactosidase may be originated from *Mortierella vinaceae* var. *raffinoseutilizer* ATCC 20034 or *Absidia griseola* ATCC 20431.

In a preferred embodiment of the present invention, soy oligosaccharide was hydrolyzed with αoy oligosaccharto obtain the sugar solution containing sucrose and galactose. Pretreatment of selective sucrose crystallization was performed to obtain the sugar solution having reduced sucrose content. Soy oligosaccharide contained excessive sucrose, so that there were disadvantages for chromatography caused by the increased volume of sugar solution, increased scale of equipment, and increased amount of purified water. Thus, the said pretreatment process of sucrose crystallization could be reduce the utility of the process.

According to the present invention, a novel technique to produce galactose or tagatose economically by using the sugar solution selectively hydrolyzed with α-galactosidase has been established. To convert galactose obtained in the present invention to tagatose, arabinose isomerase can be used.

Preferably, thermophilic arabinose isomerase originated from *Sulfurobus* sp., *Thermotoga* sp., or *Geobacillus* sp. can be used. More preferably, thermophilic arabinose isomerase originated from *Thermotoga neapolitana* DSM5068 can be used.

In this invention, the sugar solution composed of mixed sugar comprising sucrose, galactose, and tagatose obtained by hydrolysis and isomerization is separated by chromatography. More preferably, three-phase separation of chromatography is used.

In general, phase equilibrium is theoretically presented in reversible reaction such as isomerization under the economical process condition, and it is theoretically impossible to convert every substrate to a product. Therefore, in the process like the sugar process, efficient separation and recycling of non-reacted materials using chromatography are necessary. The other key point of this production technique lies on the economic execution of chromatography.

In the separation with chromatography, the resin having Ca residue can be used as the resin for the separation of sugar solution.

In the separation with chromatography, the recycling method of non-reacted materials can be randomly selected by those in the art considering the kind of sugar solution.

The sugar solution containing tagatose as a major component (at least 90%) can proceed to crystallization, if necessary, after the concentration of tagatose.

The sugar solution containing galactose as a major component can be recycled selectively before the crystallization or the isomerization considering the composition ratio of the sugar solution.

The sugar solution containing sucrose as a major component can be processed through concentration or crystallization, and then further used as sugar solution or as a raw material for other productions.

Practical and presently preferred embodiments of the present invention are illustrative as shown in the following Examples. However, it will be appreciated that those skilled in the art, on consideration of this disclosure, may make modifications and improvements within the spirit and scope of the present invention.

In a preferred embodiment of the present invention, to obtain possible raw materials for the economic production of galactose or tagatose by chromatography, sugar constituents of industrial by-products were analyzed and evaluated. Then, selective hydrolysis was performed with the selected soy bean whey or soy oligosaccharide by using α-galactosidase to prepare hydrolysate. And at last, the present inventors developed a novel technique for the economic production of galactose or tagatose from the hydrolysate. In particular, the present invention introduced continuous recycling for the above production procedure, leading to the advanced high yield economic production technique.

In the present invention, the material which was composed largely of carbohydrate and could be easily obtained from the by-products of material processing was selected as the primary raw material for the economic production of tagatose. And then, carbohydrate components, particularly soluble sugar components (including monosaccharide, disaccharide, and oligosaccharide) and contents in the material were analyzed thoroughly. From which, the present inventors confirmed the utility as a composition suitable for chromatography after being through selective hydrolysis using an enzyme.

Based on the results of the above analysis, it was confirmed that soy bean whey, the by-product of isolated soy protein and soluble sugar solution or soy oligosaccharide originated therefrom had excellent composition appropriate for pure and economic separation of galactose or tagatose. Therefore, the present inventors completed this invention by establishing the production processes of tagatose using the said raw material.

EXAMPLES

Example 1

Analysis of Sugar Composition of Industrial By-Product

The commercial soy oligosaccharide was obtained from Chinese market, which was used as a sample. HPLC was performed to analyze the composition and the content of carbohydrate included in the obtained soy oligosaccharide. The column used herein was Supelco-PB sugar separation column (SUPELCO), and purified water (0.5 ml/min) was used as a moving phase. HPLC grade reagent (Sigma) was used as the standard solution. The results are shown in Table 2.

TABLE 2

| Soy oligosaccharide composition | | |
|---|---|---|
| Sugar | Retention time (min) | Composition (dried solid base, weight %) |
| Stachyose | 12.549 | 51.7 |
| Raffinose | 13.441 | 21.8 |
| Sucrose | 14.384 | 11.9 |
| Glucose | 16.919 | 3.7 |
| Galactose | 19.783 | 6.3 |
| Fructose | 23.206 | 4.6 |

Figure 2:
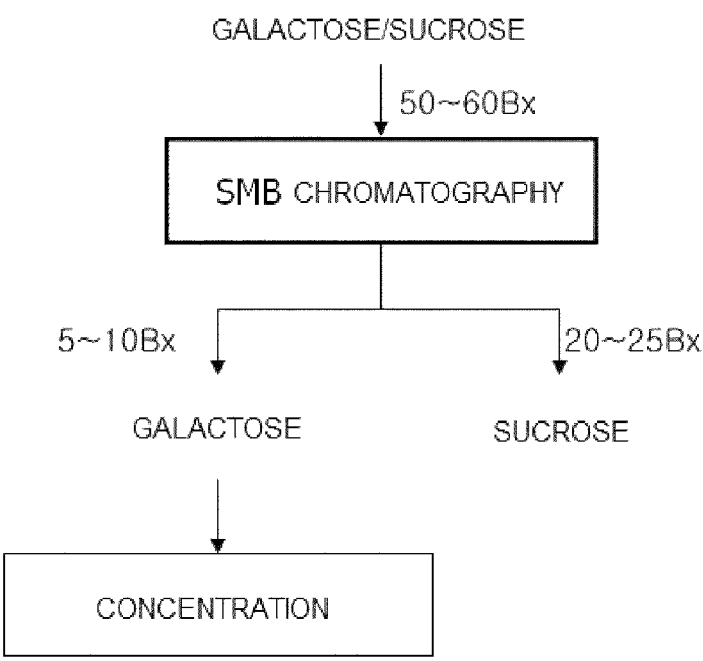

In the carbohydrate composition of soy oligosaccharide, the content ratio of raffinose and stachyose took 73.5% by the total carbohydrate, and sucrose and fructose took 26.5%. FIG. 2 illustrates HPLC chromatogram of this experiment.

Example 2

Analysis of Sugar Content in Soy Oligosaccharide and Enzyme Hydrolysis

The soy oligosaccharide of example 1 was treated with αhe soy oligosacfor the use as a galactose source. The enzyme used at this time was validase (Validase AGS; Valley Research, US) and the concentration of the enzyme was 0.15% (w/w) by the total volume of the substrate, soy oligosaccharide. Hydrolysis was performed at 50° C. with stirring at the speed of 150 rpm. The time-dependent galactose production by hydrolysis with αiththe speed ofand the changes of sugar composition are illustrated in FIG. 3.

Validase decomposed soy oligosaccharide, stachyose, into raffinose and galactose. The produced raffinose was decomposed again into sucrose and galactose. The major component of validase was α-galactosidase. It is added to feeds, because when it is added, it decomposes soy oligosaccharide, so that it reduces diarrhea, abdominal pain, and other side effects caused by soy oligosaccharide intake.

Figure 3:
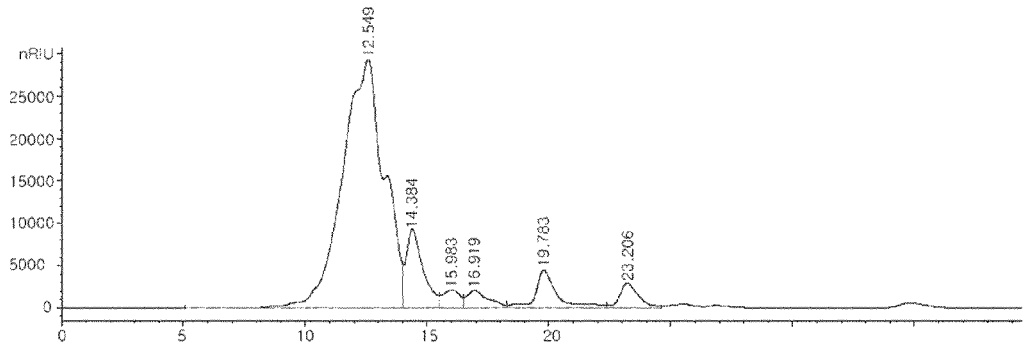
FIG. 3 is a graph showing the HPLC profile which analyzes the sugar content in soy oligosaccharide.
Figure 4:
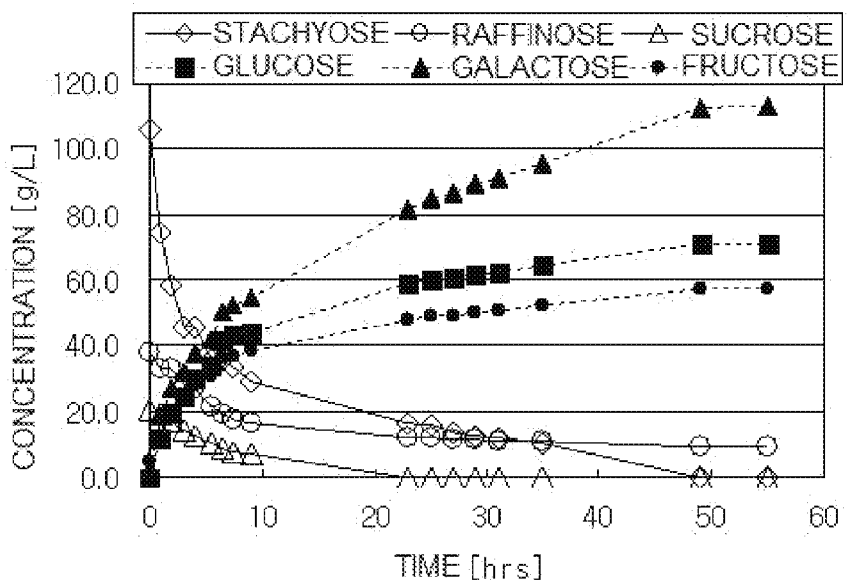
FIG. 4 is a graph showing the result of component analysis of soy oligosaccharide and the result of hydrolysis thereof.

As shown in FIG. 3, α-galactosidase in the product was functioning to hydrolyze selectively galactose/galactose bond and galactose/sucrose bond in soy oligosaccharide.

However, invertase activity functioning to decompose sucrose into glucose and fructose was also confirmed.

Sucrose was all decomposed in 24 hours, but glucose and fructose were continuously generated. This was presumably because of that sucrose produced by the decomposition of stachyose and raffinose was continuously decomposed by invertase in validase with producing glucose and fructose. After 50 hours of hydrolysis, galactose, fructose and glucose were no more generated and the sugar composition at that time is shown in Table 3.

TABLE 3

Composition of soy oligosaccharide treated with validase

| Sugar | Composition (dried solid base, weight %) |
|---|---|
| Stachyose | 0 |
| Raffinose | 3.8 |
| Sucrose | 0 |
| Glucose | 28.4 |
| Galactose | 45 |
| Fructose | 22.8 |

Example 3

Invertase Free α-Galactosidase

As described hereinbefore, selective hydrolysis of raffinose or stachyose to sucrose and galactose using an enzyme is essential not only for the convenience of chromatography but also for the economic production of tagatose. Therefore, a technique that facilitates selective cleavage of alpha-1,4 linkage between sucrose and galactose which compose raffinose or stachyose by using α-galactosidase is needed.

However, to produce an enzyme that is industrially applicable, it is general to obtain supernatant by culturing a microorganism producing the enzyme or mycelia thereof, which is then further used as a raw material for the production of the enzyme. The commercialized α-galactosidase on the market is also prepared by using the cultured supernatant of mycelia of *Aspergillus niger* as a raw material and thus most of the produced enzyme includes invertase in their enzyme solution.

Invertase, the most representative glycolytic enzyme that most living creatures in nature system have, is capable of decomposing sucrose easily. So, invertase included in an enzyme solution can hydrolyze sucrose contained in the sugar solution fast into glucose and fructose, which becomes a major obstacle to the efficient production of tagatose.

Therefore, the present inventors investigated whether or not those cells producing α-galactosidase, in many microorganisms or mycelia found in the nature, could also produce invertase, and the result is shown in Table 4.

TABLE 4

Invertase production

|  | α-galactosidase | Invertase |
|---|---|---|
| *Aspergillus niger* | 0 | 0 |
| *Aspergillus oryzae* | 0 |  |
| *Aspergillus oryzae* d-*Aspergillusniger* | 0 |  |
| *Mortereliaalla vinacea* var. Raffinose utilizer | 0 |  |
| *Absidia griseola* | 0 |  |
| *Saccharomyces carlsbergensis* | 0 | 0 |

TABLE 4-continued

Invertase production

|  | α-galactosidase | Invertase |
|---|---|---|
| *Saccharomyces cerevisiae* d-Guar seed | 0 | 0 |
| *Bacillus subtilis* |  | 0 |
| *Kluyveromyces fragilis* |  | 0 |

In this invention, cultured mycelia of *Mortierella vinaceae* var. *Raffinose utilizer* or *Absidia griseola* that produced not invertase but α-galactosidase alone was used as hydrolase.

The invertase free α-galactosidase used in this invention was originated from the fungus distributed from ATCC, *Mortierella vinaceae* var. *raffinose* utilizer ATCC20034 or *Absidia griseola* ATCC20431.

The culture medium for the selected strain was composed of 0.1M phosphate buffer (pH 6.0), 10 g/l of lactose, 3 g/l of peptone, 3 g/l of yeast extract, 0.5 g/l of potassium chloride, 0.5 g/l of magnesium sulfate, and a small amount of ferrous sulfate. The cells were cultured at 30° C. for 3 days, followed by collecting the cells using a filter system (CORNING, BOTTLE and BOTTLE TOP FILTERS). The collected cells were put in ice, followed by lysis using a homogenizer for 10 minutes. Centrifugation was performed at 10,000 rpm for 10 minutes to obtain the supernatant, the final enzyme solution.

Figure 5:
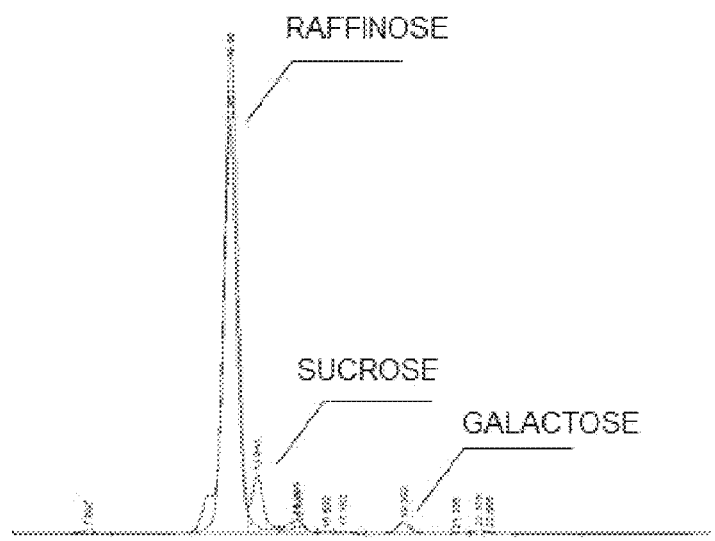
Figure 6:
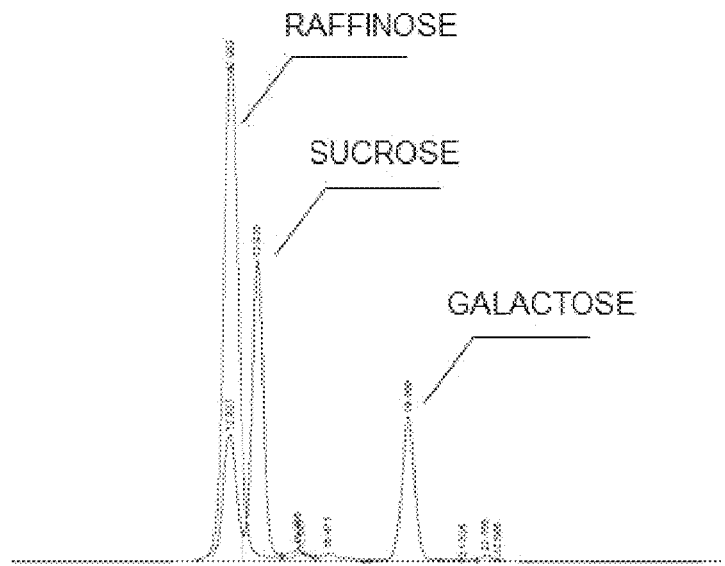

Soy oligosaccharide was hydrolyzed by using the enzyme solution obtained above. The reaction was induced at 40° C. for 7 hours. HPLC (SUPELCO, SUPELCOGEL Pb HPLC Column) was performed to analyze sugar content. As a result, it was confirmed that soy oligosaccharide was selectively hydrolyzed to sucrose and galactose by the invertase free α-galactosidase, which is displayed in FIG. 5 and FIG. 6.

Example 4

Isomerization of Galactose to Tagatose Using L-Arabinose Isomerase

The isomerization of galactose to tagatose in this invention was performed using thermophilic arabinose isomerase originated from hyperthermophilic *Thermotoga neapolitana* DSM 5068, obtained by expressing arabinose isomerase derived from hyperthermophile in *Corynebacterium* host.

The gene encoding the arabinose isomerase was inserted in the *E. coli-Corynebacterium* shuttle vectors pCJ-1 and pCJ-7 (Korean Patent NO. 10-2006-0068505) and finally the host *Corynebacterium glutamicum* KCTC 13032 was obtained. The strain in which the thermostable enzyme was expressed was mixed with 2.0% sodium alginate solution at the concentration of 20% (w/v), followed by stirring to prepare a suspension. The suspension was dropped in 0.1 M $CaCl_2$ solution by free fall to induce curing reaction. The obtained cell-captured alginate curing bead was used for immobilization. The sugar solution obtained from the reaction was added with 20 mM Tris-HCl (pH 7.5) buffer to regulate pH thereof, which was used as a substrate solution.

The prepared arabinose isomerase was used for isomerization to obtain the isomerized product.

Example 5

Analysis of Chromatography Separation Pattern of Hydrolyzed Mixed Monosaccharide To design a chromatography separation method of galactose using the isomerized product (mixed monosaccharide)

obtained from the above example, analysis of chromatography separation pattern was performed.

Figure 7:
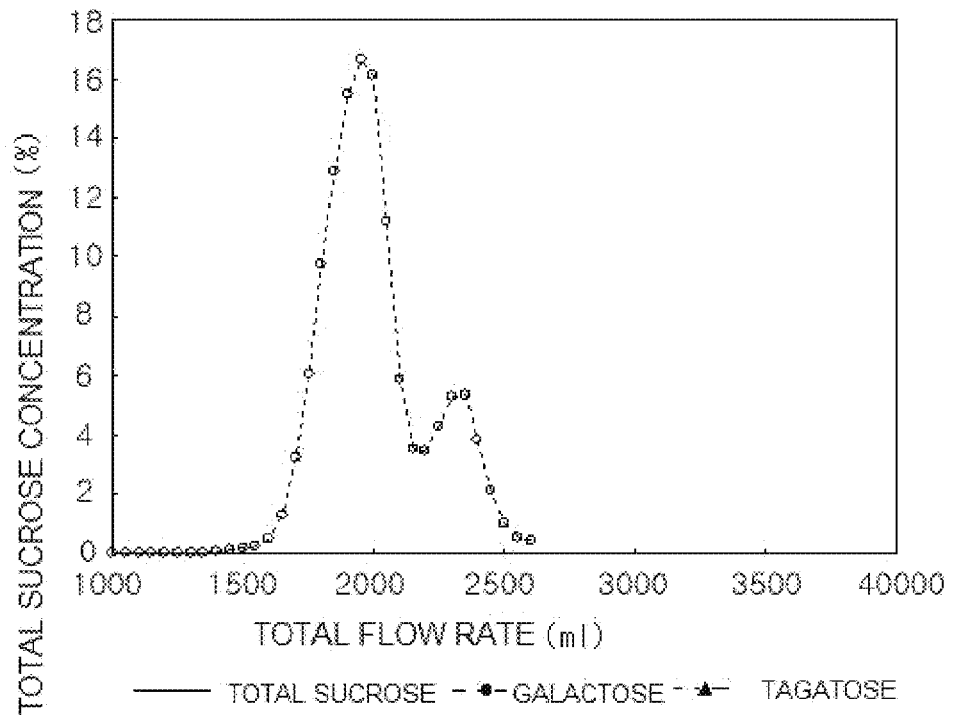
FIG. 7 and FIG. 8 illustrate the analysis of separation pattern by chromatography with mixed monosaccharide hydrolyzed previously.
Figure 8:
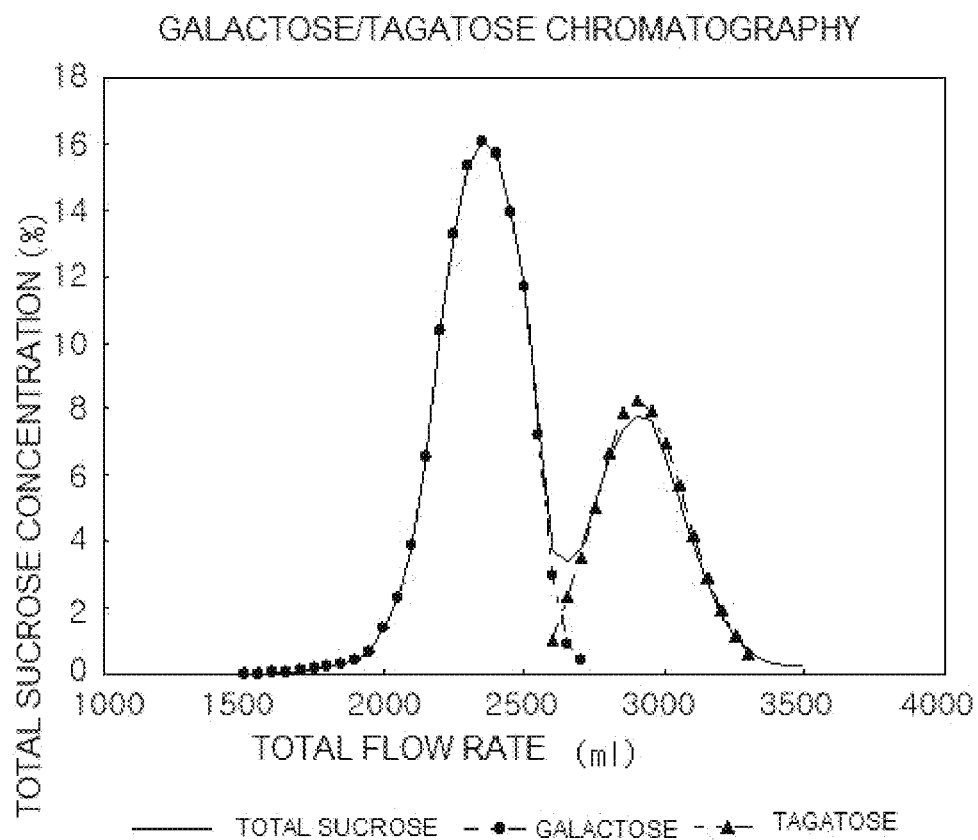

For the chromatography separation of the mixed monosaccharide, the experiment was performed with the following materials and equipments. The resin for sugar separation was FINEX MFG220 $Ca^{++}$ (FINEX). The moving phase was purified ultra pure water (11 ml/min at 60° C.). Two XK50/100 columns (Ammersham Bioscience, USA) were connected in series. The resin of each column was filled with 1900 ml. The mixed sugar used for the separation was prepared as a sugar solution at the concentration of 50 Bx, which was used by 160 ml at a time. The composition of the primary mixed monosaccharide was sucrose:galactose (80:20) and the composition of the secondary mixed monosaccharide was galactose:tagatose (50:50), followed by analysis of separation patterns. As a result, it was confirmed that sucrose, galactose, and tagatose were easily separated at a regular interval, which is shown in FIG. 7 and FIG. 8.

Example 6

Crystallization of Tagatose

Crystallization of tagatose was performed by using the recovered solution from the chromatography separation in example 5. The fraction including 90% of the final tagatose content was recovered. The fraction was concentrated in a crystallizer with vacuum and heating condition to make the sugar content 70 Bx. Then, the temperature was lowered to 50° C., slowly by 2 degrees per hour. Tagatose seed was added at the temperature of 40° C. to grow crystals.

As crystallization of tagatose progressed, the sugar concentration in the supernatant was comparatively diluted. To maintain the concentration of the diluted supernatant, vacuum concentration was continuously performed during the crystallization. That is, the concentration of the reaction supernatant was maintained at least 65 Bx during the crystallization and growing crystals.

Figure 9:
FIG. 9 and FIG. 10 illustrate the comparison of shape and size between the produced tagatose crystal and commercial sucrose under microscope (a: sucrose, b: tagatose).
Figure 10:
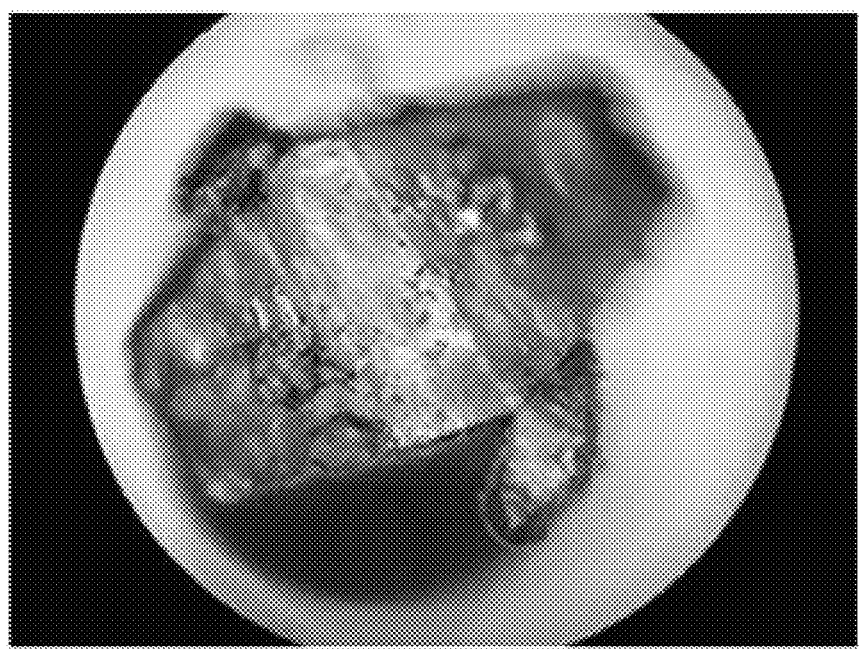

The crystallization was stopped 20 hours later. Centrifugation was performed to separate the supernatant and crystals. Tagatose recovery rate from the primary crystallization solution was 71%. The produced tagatose had at least 90 198% purity. Tagatose separated by centrifugation was dried in a vacuum drier at 50° C. for 1 hour. The generated tagatose crystal was observed under microscope, which is shown in FIG. 9 and FIG. 10. The shape and size of the generated tagatose crystal was compared with that of the commercial sucrose.

Example 7

Figure 11:
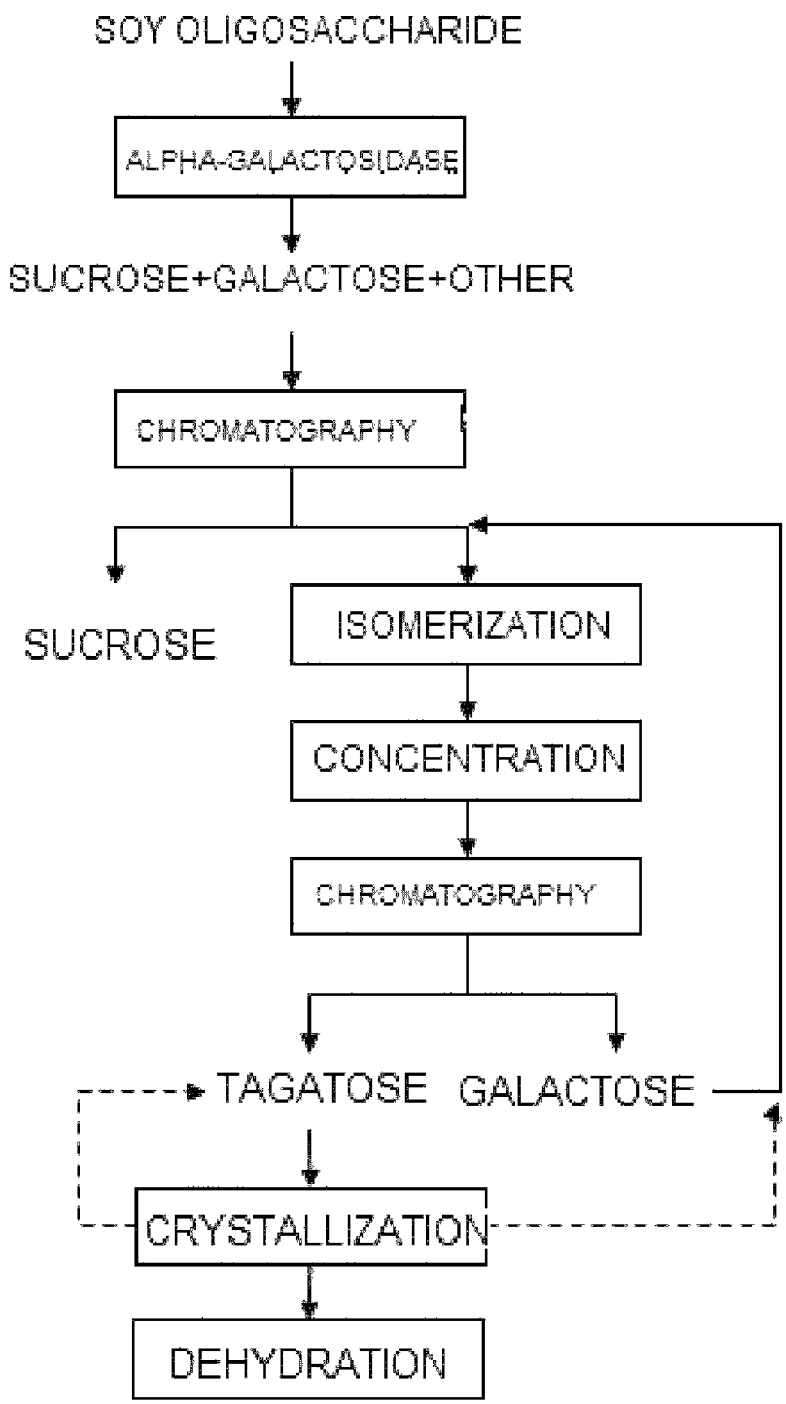
FIG. 11 illustrates the production process of tagatose using soy whey by-product or soy oligosaccharide as a raw material.

Designing Continuous Recycling Process of Tagatose Production from Soy Bean Whey Hydrolysate by Using Chromatography Separation Technique The production process of tagatose using soy bean whey or soy oligosaccharide as a raw material was designed as follows, which is shown in FIG. 11. The steps necessary for the improvement of the quality of a final product such as decolorization and desalinization are not separately included, because these steps can be included or excluded during the production process, considering the quality changes of the product.

1. separating soy oligosaccharide from by-products of soy bean whey after the pretreatment by ultrafiltration or microfiltration;

2. hydrolyzing the soy oligosaccharide solution (concentration: 10-50%) at a high or a low temperature (when the enzyme originated from thermophilic bacteria or fungi was used);

3. separating the hydrolyzed sucrose and galactose by chromatography;

Concentration step can be included or excluded according to the sugar content during the process.

4. producing tagatose by passing the chromatography separation solution containing galactose as a major component (at least 50%) through L-arabinose isomerase (or L-galactose isomerase) reactor;

5. separating the isomerized product comprising galactose, tagatose, and a small amount of mixed sugar by chromatography;

Concentration step can be included or excluded according to the sugar content during the process.

6. concentrating and crystallizing (if necessary) the chromatography separation solution containing tagatose as a major component (at least 70%);

7. recycling the remaining chromatography solution containing galactose as a major component in the isomerization reactor; and 8. recycling the non-crystallized solution obtained in the step of crystallizing tagatose back to the pre-crystallization step or pre-isomerization step, considering the composition of the sugar solution.

Example 8

Three-Phase Separation of Mixed Monosaccharide 1 pass test was performed with the sugars included in the whole process as a package. The result was used for design simulation of the continuous recycling production process using chromatography separation technique.

1 pass test was performed with mixed sugar, and basic parameters were calculated from the result. New Simulated Moving-bed System (Organo, Japan) was used and simulation test with concentration profile of each component was performed using a computer. Then, purity of each component and recovery rate of each fraction were calculated. Effluent liquid was separated from each fraction. Each fraction was analyzed by HPLC. From the result, elution curve of each component was made. Each elution pattern was examined and basic parameters of each component were calculated. Conditions for 1 pass test are shown in Table 5. Analysis method of each fraction is illustrated in Table 6. Conditions for HPLC are shown in Table 7.

TABLE 5

| Conditions for 1 pass test | |
|---|---|
| Sample | Mixed monosaccharide sample sucrose: 73.93%, others-2: 0.51% galactose: 12.62%, others-3: 0.39% Tagatose: 12.56% |
| Conc. of applying syrup | Bx. 60% |
| Absorbent | Amberlite (amberlite CR-1310; Ca-type, New resin) |
| Column size | 20 mm × 1000 mm (314 ml) |
| Desorbent | $H_2O$ |
| Applying volume | 15 ml |
| Flow rate | 26 ml/min (LV 5 m/h) |
| Temperature | 60° C. |

TABLE 6

| Analysis method | |
|---|---|
| Brix: concentration (g/100 g) | Refractometer: RA-50 (Kyoto Electronics) |
| Monosaccharide composition | HPLC: VP series (Shimadzu Corp.) |

TABLE 7

| HPLC condition | |
|---|---|
| Column | TSK-GEL SCX-Ca (6.0 × L150 × 5 column) |
| Desorbent | H$_2$O |
| Flow rate | 0.8 ml/min |
| Applying volume | 10 μl |
| Temperature | 70° C. |
| Concentration measuring device | Different refraction index meter |

Figure 12:
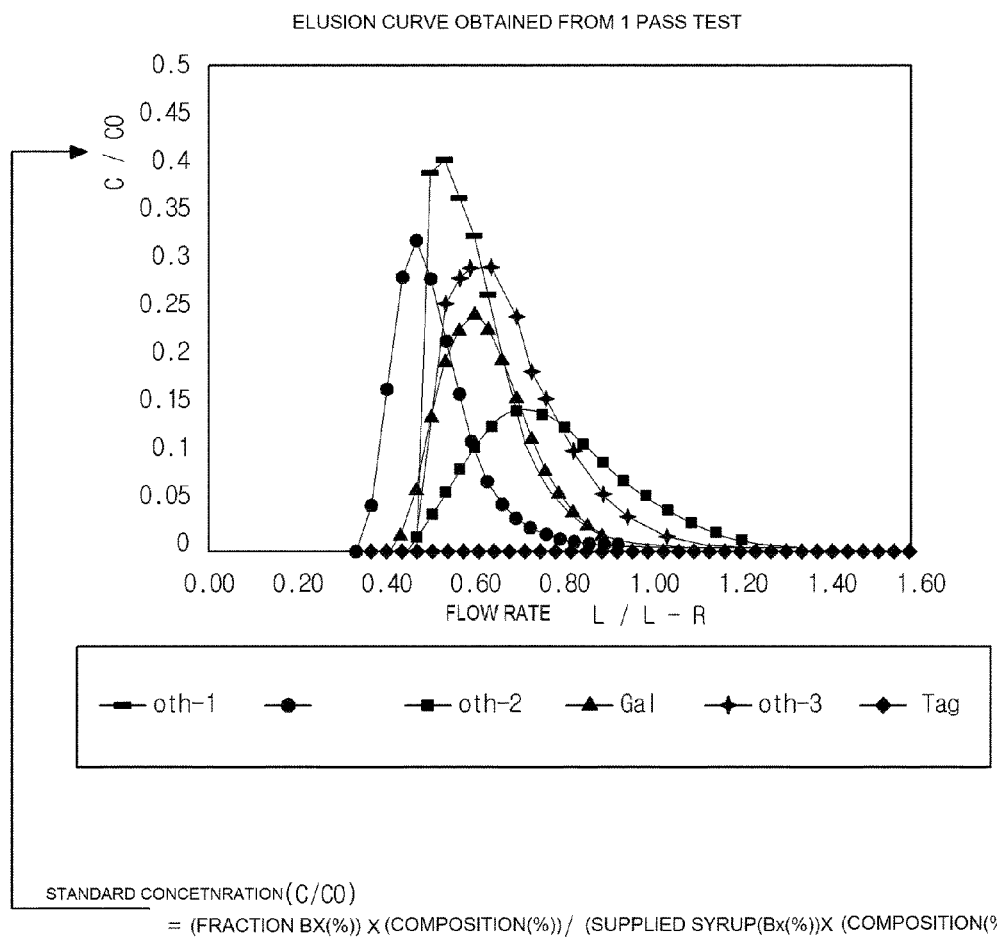
FIG. 12 illustrates the elution curve obtained from 1 pass test.

Elution curve obtained from the 1 pass test is shown in FIG. 12.

Figure 13:
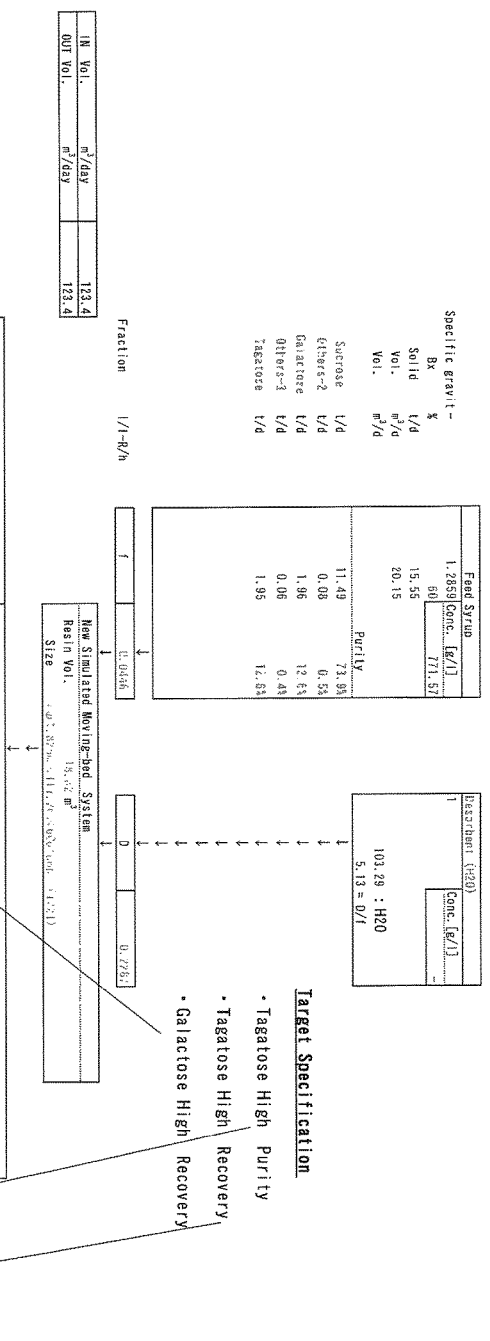
FIG. 13 illustrates the detail drawing of case 9 (3 phase separation) simulation.

Basic parameters were calculated from the elution curve and computer simulation was performed to calculate separation performance. The conditions for the simulation are shown in Table 8. To obtain optimum separation performance, the inventors analyzed sugar composition of the total solution with changing the ratio of the sample sugar solution to the moving phase, water (desorbent/applying volume). Recovery rate of each sugar and purity thereof were measured from the analysis. The result of the simulation is summarized in Table 9. As shown in Table 9, cases #6, #7, #8, and #9 are mass balance sheets obtained from the result of the simulation. Tagatose demonstrated at least 90% purity as wanted in each simulation. The detailed diagram of the result of the simulation of case #9 is shown in FIG. 13.

TABLE 8

| Simulation condition | |
|---|---|
| Condition | 3 phase separation |
| Conc. of applying syrup | Bx 60 |
| Target purity | Purity of tagatose: at least 90% |
| Result | Case 6  Case 7  Case 8  Case 9 |

TABLE 9

Summary of simulation results

| Condition | Case 6 | Case 7 | Case 8 | Case 9 |
|---|---|---|---|---|
| Flow rate (L/L-R/hr) | 0.0464 | 0.0469 | 0.0469 | 0.0446 |
| Desorbent/applying volume | 4.93 | 4.91 | 5.31 | 5.13 |
| Tagatose purity (%) | 95.2 | 93.6 | 96.0 | 97.2 |
| Tagatose recovery rate (%) | 87.8 | 91.1 | 81.7 | 93.0 |
| Galactose purity (%) | 74.3 | 76.3 | 63.7 | 77.8 |
| Galactose recovery rate (%) | 88.5 | 86.0 | 98.3 | 92.7 |

The performance explained in this example was calculated by Organo computer simulation.

Example 9

Reaction Stability of L-Arabinose Isomerase in Mixed Monosaccharide

In the economic tagatose production process using three-phase chromatography proposed in this invention, the substrate solution is mostly composed of other sugars than galactose, for example glucose, fructose, and sucrose, unlike the conventional isomerization from galactose to tagatose. So, it is an important condition for introduction of the technique of the present invention whether or not those different sugars could inhibit isomerization using enzymes. In this example, the present inventors tried to disclose substrate specificity of galactose isomerization in the mixed monosaccharide solution when the isomerase selected by the inventors was used.

Each substrate solution was prepared by adding sucrose, glucose, and fructose to 100 g/L of galactose solution at a certain ratio. The composition ratio of each sugar was as follows: (a) Suc:Glu:Gal:Fru=0:0:1:0, (b) Suc:Glu:Gal:Fru=3:1:1:1, (c) Suc:Glu:Gal:Fru=0:3:1:2. Each sugar ratio was regulated as similar to those of (a) the control group containing galactose only, (b) the group in which 1,4-linkage of galactose in oligosaccharide was selectively hydrolyzed, and (c) the group in which sugars were completely hydrolyzed to monosaccharides.

For galactose isomerization, pellet of the deposited strain (CJ-1-TNAI, Accession No: KCCM10786P) raised in the expression medium was added to the substrate solution at the concentration of 10% (w/v), followed by reaction at 70° C. for 1 hour. Upon completion of the reaction, the mixed solution was cooled down at 4° C. for 15 minutes, followed by centrifugation at 12,000 rpm for 15 minutes to obtain supernatant. The obtained supernatant was 5-fold diluted with purified water, which passed through 0.45 an syringe filter (Millipore, USA), followed by HPLC analysis.

Figure 14:
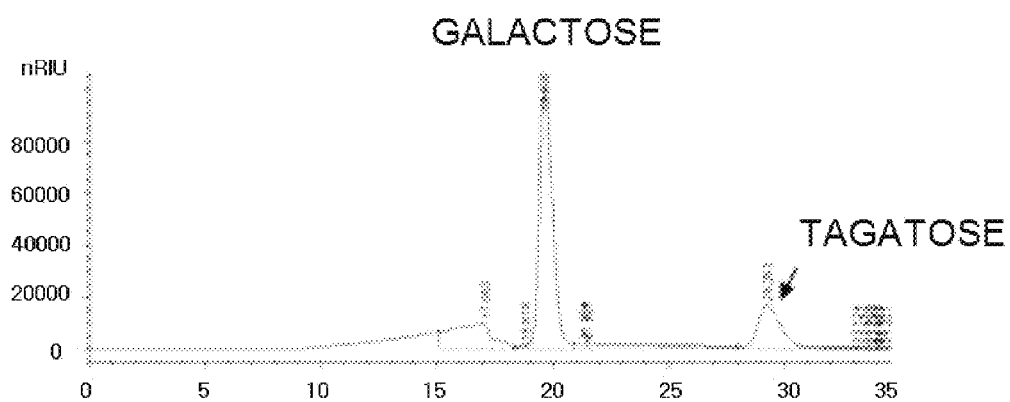
FIG. 14, FIG. 15, and FIG. 16 illustrate the sugar contents of the isomerized product in mixed monosaccharide solution analyzed by HPLC.
Figure 15:
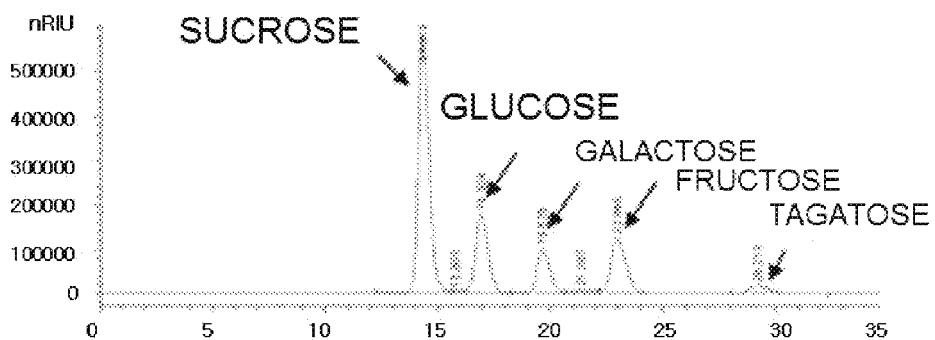
Figure 16:
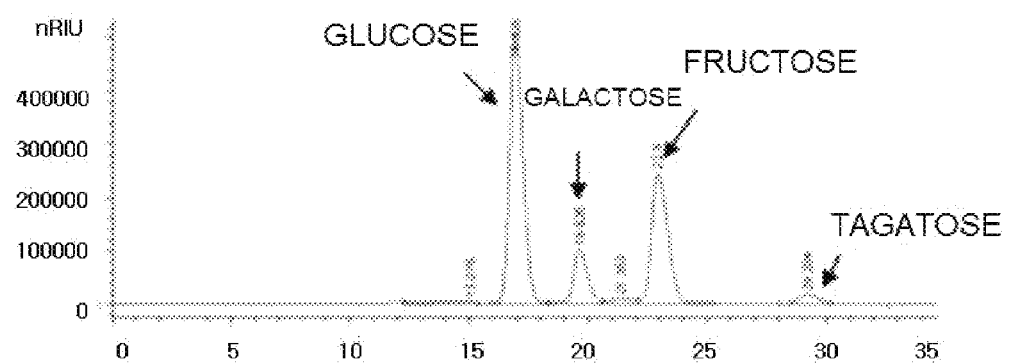

Sugar concentration in the isomerized product in the mixed monosaccharide solution was analyzed by HPLC. The results are shown in FIG. 14 and FIG. 16. The concentration of each sugar was quantified with each standard solution and the results are shown in Table 10.

TABLE 10

| | Sucrose (g/L) | Glucose (g/L) | Galactose (g/L) | Fructose (g/L) | Tagatose (g/L) |
|---|---|---|---|---|---|
| (a) Control group | 0 | 0 | 13.4 | 0 | 5.9 |
| (b) Condition 1 | 54.7 | 21.3 | 13.5 | 0 | 6.0 |
| (c) Condition 2 | 0 | 60.4 | 13.7 | 37.2 | 6.0 |

As a result, it was confirmed that galactose isomerization in the mixed sugar solution comprising a large amount of sucrose, glucose, and fructose was not affected and the reaction speed remained the same to give the consistent conversion rate (reached to the same conversion rate, 30.8%). Therefore, it was confirmed that glucose, fructose, and sucrose obtained by hydrolysis of raw materials originated from soy oligosaccharide did not act as an obstacle for the galactose isomerization.

Example 10

Designing of Continuous Recycling Tagatose Production Process from Hydrolysate of Soy Bean Whey Using Three-Phase Separation Technique The tagatose production process designed in example 6 is characterized by two times of chromatography which requires a huge amount of purified water and concentration. In this invention, to overcome the said inconvenience, the present inventors designed a new tagatose production method that only requires one time chromatography, which could be realized by the advanced chromatography design. This has been proved and illustrated in detail in the above example.

Figure 17:
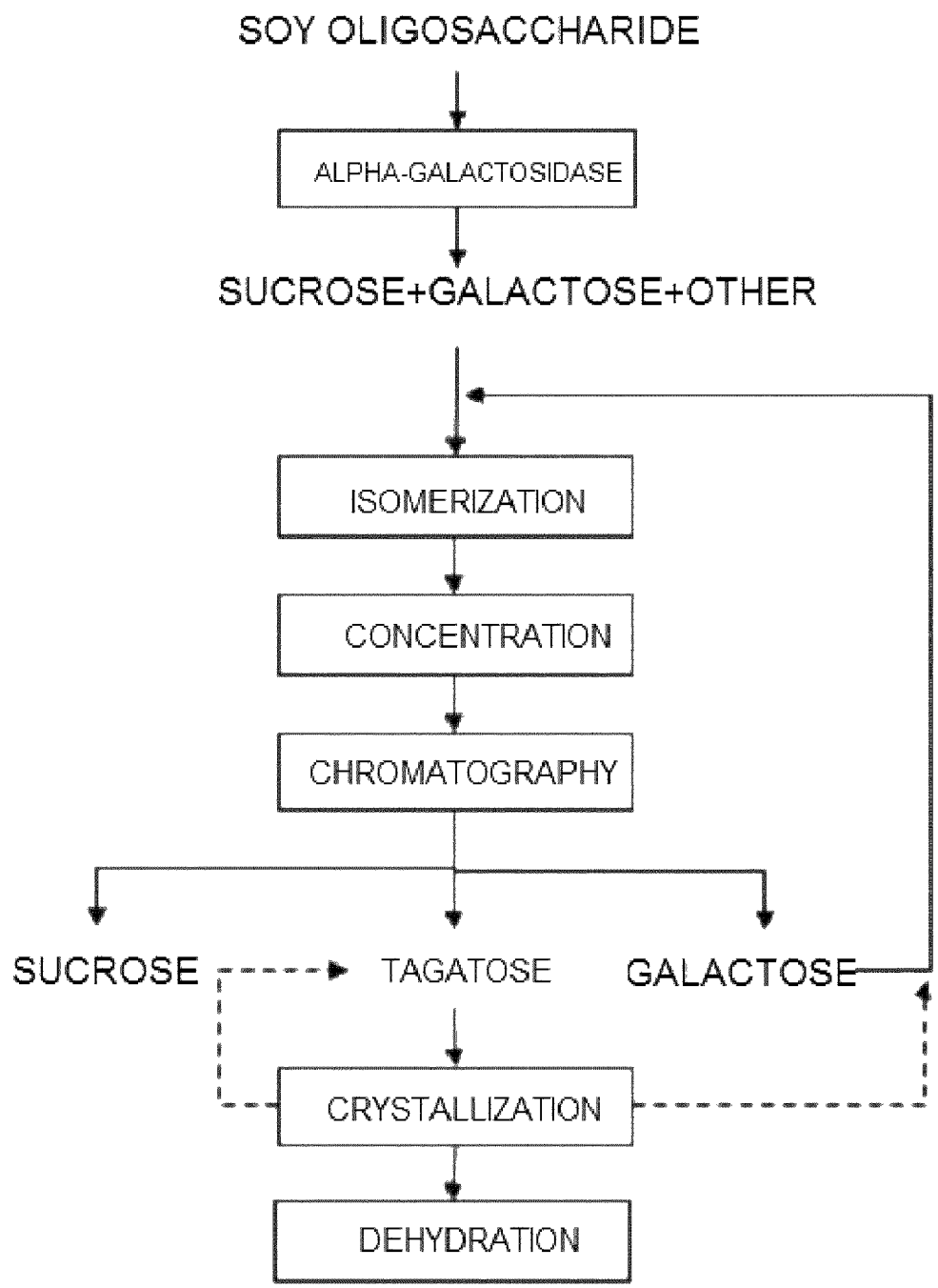
FIG. 17 is a simple diagram illustrating the production process of tagatose using single chromatography.

The tagatose production process using a single chromatography was designed as follows, which is briefly illustrated in FIG. 17. The steps necessary for the improvement of the quality of a final product such as decoloriatino and desalinization are not separately included, because these steps can be included or excluded during the production process, considering the quality changes of the product.

1. separating soy oligosaccharide from by-products of soy bean whey after the pretreatment by ultrafiltration or microfiltration;

2. hydrolyzing the soy oligosaccharide solution (concentration: 10-50%) at a high or a low temperature (if the enzyme originated form thermophilic bacteria or fungi was used);

3. isomerizing galactose to tagatose by passing the hydrolyzed sugar solution containing sucrose and galactose as major components (at least 90%) through L-arabinose isomerase (or L-galactose isomerase) reactor;

4. separating the isomerized solution composed of the mixed sugar containing sucrose, galactose, and tagatose as major components (at least 90%) by three-phase chromatography;

Concentration step can be included or excluded according to the sugar content during the process. The sugar separation solutions obtained from the chromatography above were the following three solutions:

A. Chromatography separation solution comprising tagatose as a major component (at least 90%), which can be proceed to concentration (if necessary) and crystallization.

B. Chromatography remaining solution comprising galactose as a major component, which can be recycled to the pre-isomerization step or pre-crystallization step, considering the composition of the sugar solution.

C. Chromatography remaining solution comprising sucrose as a major component, which can proceed to concentration and crystallization further to be processed as sucrose solution, or can be used as an advanced raw material for the production of another product.

5. recycling the non-crystallized solution obtained in the step of crystallizing tagatose back to the pre-crystallization step or pre-isomerization step, considering the composition of the sugar solution.

Example 11

Designing of Continuous Recycling Tagatose Production Process from Hydrolysate of Soy Bean Whey Using Sucrose Crystallization Pretreatment By taking one step further from the advanced tagatose production method using a single chromatography explained above, the present inventors designed to reduce process utility by reducing sucrose content in the sugar solution via sucrose crystallization.

Soy oligosaccharide contains excessive sucrose, which increases the volume of sugar solution for chromatography separation, increases equipment scale, and increases consumed purified water.

Figure 18:
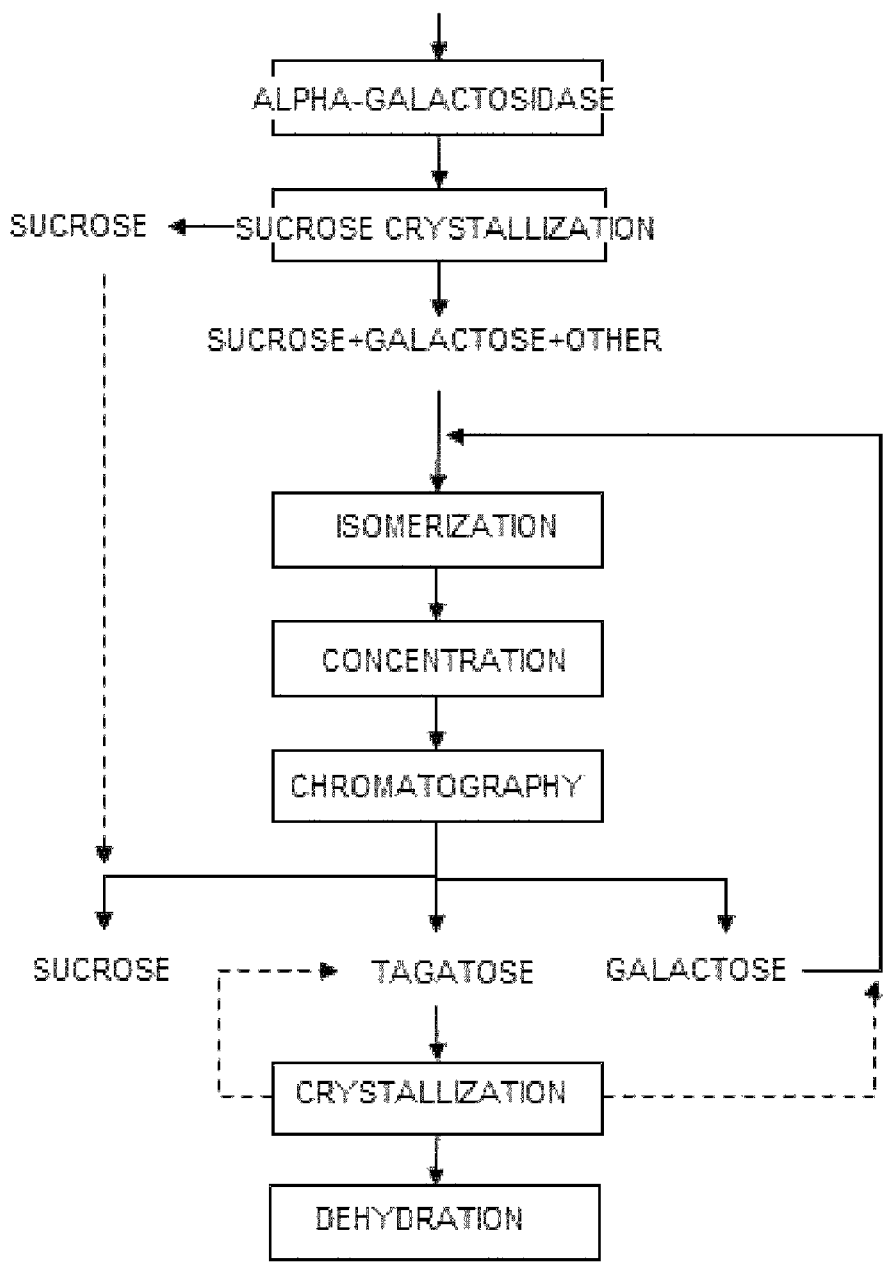
FIG. 18 is a simple diagram illustrating the production process of tagatose using single chromatography containing the step of crystallization of sucrose as the pre-treatment step.

So, the present inventors designed the tagatose production process using a single chromatography which included sucrose crystallization as a pretreatment step as follows. This process is illustrated in FIG. 18 briefly. The steps necessary for the improvement of the quality of a final product such as decolorization and desalinization are not separately included, because these steps can be included or excluded during the production process, considering the quality changes of the product.

1. separating soy oligosaccharide from by-products of soy bean whey after the pretreatment by ultrafiltration or microfiltration;

2. hydrolyzing the soy oligosaccharide solution (concentration: 10-50%) at a high or a low temperature (if enzyme originated from thermophilic bacteria or fungi was used);

3. obtaining sugar solution containing increased galactose by crystallization of sucrose in the hydrolyzed oligosaccharide solution;

4. isomerizing galactose to tagatose by passing the hydrolyzed sugar solution containing sucrose and galactose as major components (at least 90%) through L-arabinose isomerase (or L-galactose isomerase) reactor;

5. separating the isomerized solution composed of the mixed sugar comprising sucrose, galactose, and tagatose as major components (at least 90%) by three-phase chromatography;

Concentration step can be included or excluded according to the sugar content during the process. The sugar separation solutions obtained from the chromatography above were the following three solutions:

A. Chromatography separation solution comprising tagatose as a major component (at least 90%), which can be proceed to concentration (if necessary) and crystallization.

B. Chromatography remaining solution comprising galactose as a major component, which can be recycled to the pre-isomerization step or pre-crystallization step, considering the composition of the sugar solution.

C. Chromatography remaining solution comprising sucrose as a major component, which can be proceed to concentration and crystallization further to be processed as sucrose solution, or can be used as an advanced raw material for the production of another product.

6. recycling the non-crystallized solution obtained in the step of crystallizing tagatose back to the pre-crystallization step or pre-isomerization step, considering the composition of the sugar solution.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for producing tagatose, comprising the steps of:
    a) separating a solution comprising soy oligosaccharide from soybean whey;
    b) hydrolyzing the solution comprising the soy oligosaccharide with invertase-free α-galactosidase;
    c) isomerizing the resultant solution comprising hydrolyzed soy oligosaccharide from step (b) with arabinose isomerase to obtain to obtain an isomerized product comprising a mixed sugar solution containing sucrose, galactose and tagatose as the major components; and
    (d) separating the sugars in the isomerized mixed sugar solution by chromatography.

2. The method for producing tagatose according to claim 1, further comprising the step of reducing the content of sucrose in the mixed sugar solution, by crystallization of sucrose from the hydrolyzed solution comprising the soy oligosaccharide prior to performing step c).

3. The method for producing tagatose according to claim 1, further comprising the step of recycling galactose isolated from step d).

4. The method for producing tagatose according to claim 3, wherein the galactose is recycled to step b) or step c).

5. The method for producing tagatose according to claim 1, wherein the soybean whey is pretreated by ultrafiltration or microfiltration.

6. The method for producing tagatose according to claim 1, wherein the concentration of the soy oligosaccharide is 10 to 50%.

7. The method for producing tagatose according to claim 1, wherein the hydrolysis is performed at 40° C. to 80° C.

8. The method for producing tagatose according to claim 1, wherein the α-galactosidase is originated from *Mortierella vinaceae* var. *rafinoseutilizer* ATCC 20034 or *Absidia griseola* ATCC 20431.

9. The method for producing tagatose according to claim 1, wherein the α-galactosidase is able to selectively digest α-1,4 linkage between sucrose and galactose.

10. The method for producing tagatose according to claim 1, wherein sucrose and galactose are obtained by the hydrolysis of step b).

11. The method for producing tagatose according to claim 1, wherein the arabinose isomerase is originated from thermophilic *Thermotoga neapolitana* DSM 5068.

12. The method for producing tagatose according to claim 1, wherein sucrose, galactose and tagatose together comprise at least 90% of the isomerized solution.

13. The method for producing tagatose according to claim 1, wherein the chromatography of step d) is single chromatography.

14. The method for producing tagatose according to claim 13, wherein the chromatography of step d) is performed using with a resin containing $Ca^{2+}$ residues.

15. The method for producing tagatose according to claim 1, wherein the reactions of step b) to step c) are performed in the same reactor simultaneously.

16. The method for producing tagatose according to claim 2, further comprising the step of recycling the galactose isolated after step d).

17. A method for producing tagatose, comprising the steps of:
a) separating a solution comprising soy oligosaccharide from soybean whey;
b) hydrolyzing the solution comprising the soy oligosaccharide with invertase free α-galactosidase, to obtain a hydrolyzed sugar solution comprising a mixture of sucrose and galactose;
c) separating the mixture of sucrose and galactose from the remainder of the hydrolyzed sugar solution by chromatography;
d) isomerizing the mixture containing galactose and sucrose obtained from step c) with arabinose isomerase; and
e) obtaining tagatose by separating the product obtained in step d) using chromatography.

18. The method for producing tagatose according to claim 17, further comprising the steps of recycling the galactose obtained after step d) and isomerizing said recycled galactose according to step d).

* * * * *